United States Patent [19]
Shifrin et al.

[11] Patent Number: 5,476,471
[45] Date of Patent: Dec. 19, 1995

[54] DEVICE AND METHOD FOR EXTERNAL CORRECTION OF INSUFFICIENT VALVES IN VENOUS JUNCTIONS

[75] Inventors: Edward G. Shifrin, Raanana; Isaak M. Portnoy, Cfam-Sava; Solomon W. Zelmanov, Batgalim; Gennady S. Nickelshpur, Haifa; Baruch A. Morag, Ramat Gon, all of Israel

[73] Assignee: Mind - E.M.S.G. Ltd, Raanana, Israel

[21] Appl. No.: 227,883

[22] Filed: Apr. 15, 1994

[30] Foreign Application Priority Data

Aug. 19, 1993 [IL] Israel .......... 106738

[51] Int. Cl.⁶ .......... A61B 17/04
[52] U.S. Cl. .......... 606/151; 600/37; 623/66
[58] Field of Search .......... 606/151, 153; 623/1, 2, 11, 12, 17, 66; 600/36, 37

[56] References Cited

U.S. PATENT DOCUMENTS

| | | | |
|---|---|---|---|
| 4,204,282 | 5/1980 | Bolt | 623/11 |
| 4,531,519 | 7/1985 | Dunn et al. | |
| 4,586,501 | 5/1986 | Claracq | |
| 4,938,765 | 7/1990 | Rasmusson | 606/158 |
| 5,080,095 | 1/1992 | Tungate | |
| 5,100,422 | 3/1992 | Berguer et al. | 606/151 |
| 5,120,300 | 6/1992 | Shaw | 602/61 |
| 5,156,619 | 10/1992 | Ehrenfeld | 623/12 |
| 5,160,338 | 11/1992 | Vincent | 606/157 |
| 5,171,252 | 12/1992 | Friedland | |
| 5,258,027 | 11/1993 | Berghaus | 623/12 |

FOREIGN PATENT DOCUMENTS 1768154  10/1992  U.S.S.R. .......... 623/11

Primary Examiner—Gary Jackson
Attorney, Agent, or Firm—Lowe, Price, LeBlanc & Becker

[57] ABSTRACT

A compression device for external correction of insufficient valves in venous junctions is adapted for placement around the junction. The compression device has a band encompassing at least two veins of the junction. The band has a different rigidity and compression force in a direction extending from its proximal end to its distal end. The band is formed with a main compressing portion disposed on a vein surface of the junction around an insufficient valve. Intermediate and fastening portions of the band are also disposed on the vein surfaces adjacent the main compression compressing portion. The band is preferably shaped as a Mobius band. A method for external correction of insufficient valves in venous junctions is also disclosed.

22 Claims, 4 Drawing Sheets

DEVICE AND METHOD FOR EXTERNAL CORRECTION OF INSUFFICIENT VALVES IN VENOUS JUNCTIONS

FIELD OF THE INVENTION

The present invention relates to medical techniques and in particular to vein valves correction, applied in the treatment of cardiovascular diseases.

1. Background of the Invention

Varicose veins in lower limbs is one of the most common vascular diseases.

In most cases it occurs due to insufficiency of the Sapheno-Femoral Junction (SFJ)

In different countries of the World, on the average, from 40% to 60% of the female population are affected by lower limb varicosity.

It is also very important to save these veins for potential application thereof in aorto-coronary bypass or peripheral arterial reconstructions.

So far no efficient methods have been developed for the elimination of valve insufficiency and saving the superficial and deep veins, especially in the SFJ area.

The simplest and most effective solution to the problem is external compression of the vein around the insufficient valve to reduce the central opening lumen and restore valve function thereof.

There are many engineering solutions applied in medicine for correcting defects in blood vessels and human hollow organs.

Devices and methods are known for reconstructions of effected blood vessels (U.S. Pat. No. 5,100,422; or "VENOUS DISORDERS" by John B. BERGAN and James S. T. YAO, W. B. SAUNDERS COMPANY, Philadelphia, 1991, p. 303–311).

Devices are also known for compression of vessels or hollow organs or securing portable medical instruments thereon (U.S. Pat. No. 5,160,338; U.S. Pat. No. 5,080,095; U.S. Pat. No. 5,171,252 or U.S. Pat. No. 4,938,765).

Such devices can compress the vein around the insufficient valve and control, within certain limits, the compression force.

However, these devices cannot be disposed directly on a venous junction, and they do not provide the desired accuracy in compression rate control.

Special devices are further known for occluding the vein (U.S. Pat. No. 4,586,501 or U.S. Pat. No. 4,531,519) applied in surgery. They provide a more accurate control of the vein compression rate.

However, they cannot be secured directly on the venous junction. Besides, they are complex in design (with a remote pressure source) and relatively large-sized, so they cannot constantly and independently operate inside the human body.

2. The Prior Art

Most similar to the present invention is the device disclosed in U.S. Pat. No. 5,120,300 and in the book "Plastic and reconstructive operations on great veins", by A. N. Vedensky, "Medizina", Leningrad, 1979, p. 186–194.

Such devices comprise bands (U.S. Pat. No. 5,120,300) or spiral springs formed of plastic, metal, alloy or plastic reinforced with metal (lavsan, fluorineplastic etc.).

The common drawbacks of said devices as well as of those described above are as follows:

1) they cannot be applied for correction of vein valves, disposed in the venous junctions;
2) they have only a compressing portion whereas no fixing means is provided to prevent axial displacement of the compressing member along the vein.

Besides, in some cases not only the valve correction in the venous junction is required by an additional correction of the insufficient vein area adjoining said junction.

An object of the present invention is to provide a device and method for a controlled correction of an insufficient valve immediately in the venous junction, and, if necessary, of the insufficient valve in the area adjoining said junction.

SUMMARY OF THE INVENTION

An object of the present invention is a device and method for external correction of insufficient valves in venous junctions.

The claimed compression device for external correction of insufficient valves in venous junctions is adapted to placing substantially around a junction with insufficient valves in abutting contact with a desired area of said junction surface. It is formed substantially as band encompassing at least two veins of said junction and possessing different rigidity and compressing force in the direction from its proximal end to its distal end.

Said device comprises at least one main compressing portion disposed on the surface of said junction around the insufficient valve, an intermediate and a fastening portion, as well as a means for protecting the vein surface from injury made as a plastic coating. Said band is shaped as a Mobius band.

The band has at least one additional compressing portion adjoining said main compressing portion near its free end, the additional compressing portion being disposed on the insufficient vein around at least another insufficient valve near said junction.

The claimed device can comprise a main and additional compressing portion each shaped as a bifurcated or branched end of said band.

The device may be formed as a plastic coated metal or alloy band encompassing at least two veins of said junction and possessing different rigidity and compressing force in the direction from its proximal end to its distal end. In this embodiment said device has at least one main compressing portion disposed on said junction surface around the insufficient valve, an intermediate and a fastening portion. The main compressing portion of said band is shaped as a Mobius band.

In this version said band also has at least one additional compressing portion adjoining said main compressing portion near its free end, the additional compressing portion being disposed on the insufficient vein around at least another insufficient valve near said junction and formed as semirigid or resilient exovascular framework supporting and compressing the vein, said framework having a supporting member disposed substantially along the vein longitudinal axis and compressing ribs extending therefrom and provided with a means for fastening them together, such as male and female connectors.

Said main and/or additional compressing portion are formed as a bifurcated or branched end of said band.

The band can be made of a metal with a spring effect of a shape memory alloy. It can also be coated with a "Gore-tex" type plastic.

The compression device for external correction of insufficient valves in venous junctions adapted to placing substantially around a junction with insufficient valves abutting the desired area of said junction surface can be formed as a band of at least two layers of a flexible fluid-impermeable plastic peripherally sealed together and forming a cavity having at least one hermetically isolated chamber.

The band encompasses at least two veins of said junction and possesses different rigidity and compressing force in the direction from its proximal end to its distal end.

Said device comprises a band with at least one main compressing portion disposed on said junction surface around an insufficient valve, an intermediate portion and a fastening portion, as well as a means for filling said band cavity. At least one of said plastic layers in said band is reinforced with metal or shape memory alloy.

In the described compression device said main compressing portion of said band is shaped as a Mobius band comprising at least two layers of a flexible fluid-impermeable plastic, peripherally sealed together and forming cavity having on e or several hermetically isolated chambers, at least one of said plastic layers being reinforced with metal or alloy.

A quickly solidifying biologically inert fluid or biologically inert gas is applied as said means for filling said band cavity.

In this version the band can be made of a plastic reinforced with metal, such as a "Gore-tex" type plastic.

The band has at least one additional compressing portion adjoining said main compressing portion near its free end, the additional compressing portion being disposed on the insufficient vein around at least another insufficient valve near said junction and formed at least of one plastic layer, at least one layer of said additional compressing portion being reinforced with metal. The additional compressing portion can have at least two plastic layers peripherally sealed together to form a cavity having at least one hermetically isolated chamber.

In this embodiment said main and/or additional compressing portion can be shaped as a bifurcated or branched end of said band.

In this embodiment said additional portion can also be formed as a semirigid or resilient exovascular framework supporting and compressing the vein, said framework having a supporting member disposed substantially along the vein longitudinal axis and compressing ribs extending therefrom, provided with a means for fastening them together, such as male and female connectors.

The claimed method for external correction of insufficient valves in venous junctions comprise exposing, by routine technique, the venous junction, placing the correction device on said venous junction outside, so that the main compressing portion may be close to the junction and fully encompass the vein on the outside around the insufficient valve, and the fastening portion be disposed substantially on the adjacent vein.

Then the blood reflux in the vein is tested and from the reflux value the required compression of the vein with an insufficient valve is determined.

Afterwards a gradual vein compression is performed until the reflux disappears, by injecting a portion of a biologically inert gas or a quickly solidifying biologically inert fluid into hermetically isolated chambers of said band inner cavity.

Subsequently the effect is checked and, if necessary, the manipulation is repeated, increasing or reducing compression in certain band chambers.

Then the need in applying the additional compressing portion of said band is determined as well as the required compression rate. When application of the additional compressing portion is necessary, it is disposed and fastened in a known manner on the vein around another or several other insufficient valves, adjusting the compression rate and length of said compressing portion, cutting off its redundant piece and fastening together in a certain manner the available connectors of the remaining piece ribs.

When the application of said additional compressing portion is not necessary, the latter is completely cut off.

And, in the end, the final correction effect is checked, determining the blood reflux in the whole venous junction being corrected, and the wound is closed by routine surgical technique.

BRIEF DESCRIPTION OF DRAWINGS

The above and other objects, features and advantages of the present invention will become more readily apparent from the following description, reference being made to the accompanying drawings in which.

SPECIFIC DESCRIPTION

Figure 1:
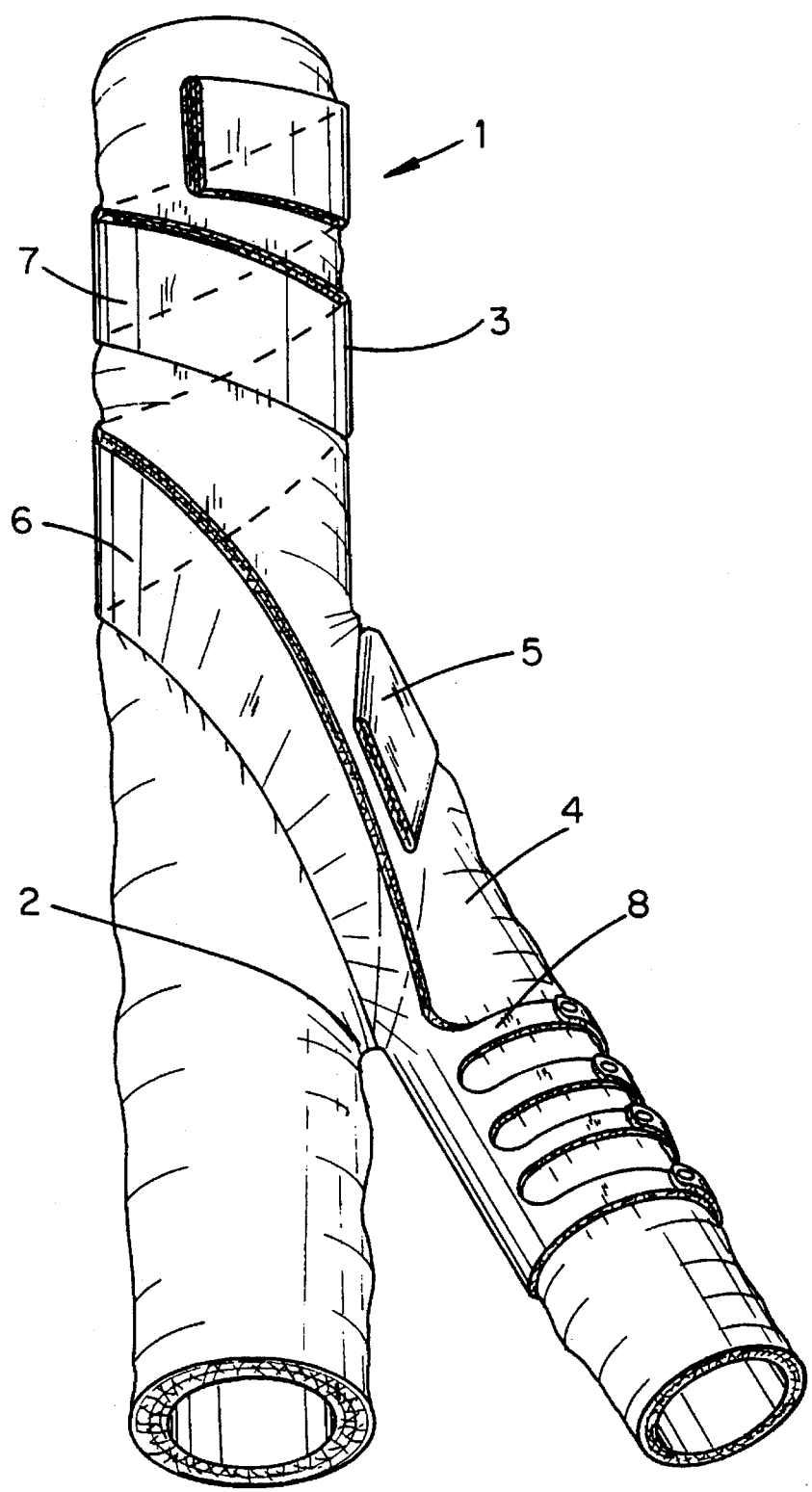
FIG. 1 is a general view of the claimed device disposed on a venous junction formed of plastic coated metal band.

According to the present invention the compression device 1 for external correction of insufficient valves in venous junctions 2 is shaped as a band 3 formed of metal or alloy. Said band encompasses at least two veins 4 of said junction 2 and possesses different rigidity and compressing force in the direction from its proximal end to its distal end.

The band 3 compresses a main compressing portion 5 disposed on the surface of said junction 2 around an insufficient valve (not shown in the drawing), an intermediate 6 and a fastening 7 portion, as well as a means for protecting the vein surface formed as a plastic coating. Said band 3 is shaped as a Mobius band.

Said band 3 also has an additional compressing portion 8 adjoining the main compressing portion 5 near its free end, said additional compressing portion 8 being disposed on the insufficient vein 4 around at least another insufficient valve (not shown in the drawing) near said junction 2 (see FIG. 1).

An embodiment of the claimed device is possible where said main 5 and/or additional 8 compressing portion is shaped as a bifurcated or branched end of said band 3.

The band 3 can be formed of metal with a spring effect or a shape memory alloy.

The band 3 may be as well coated with a "Gore-tex" type plastic.

Figure 2:
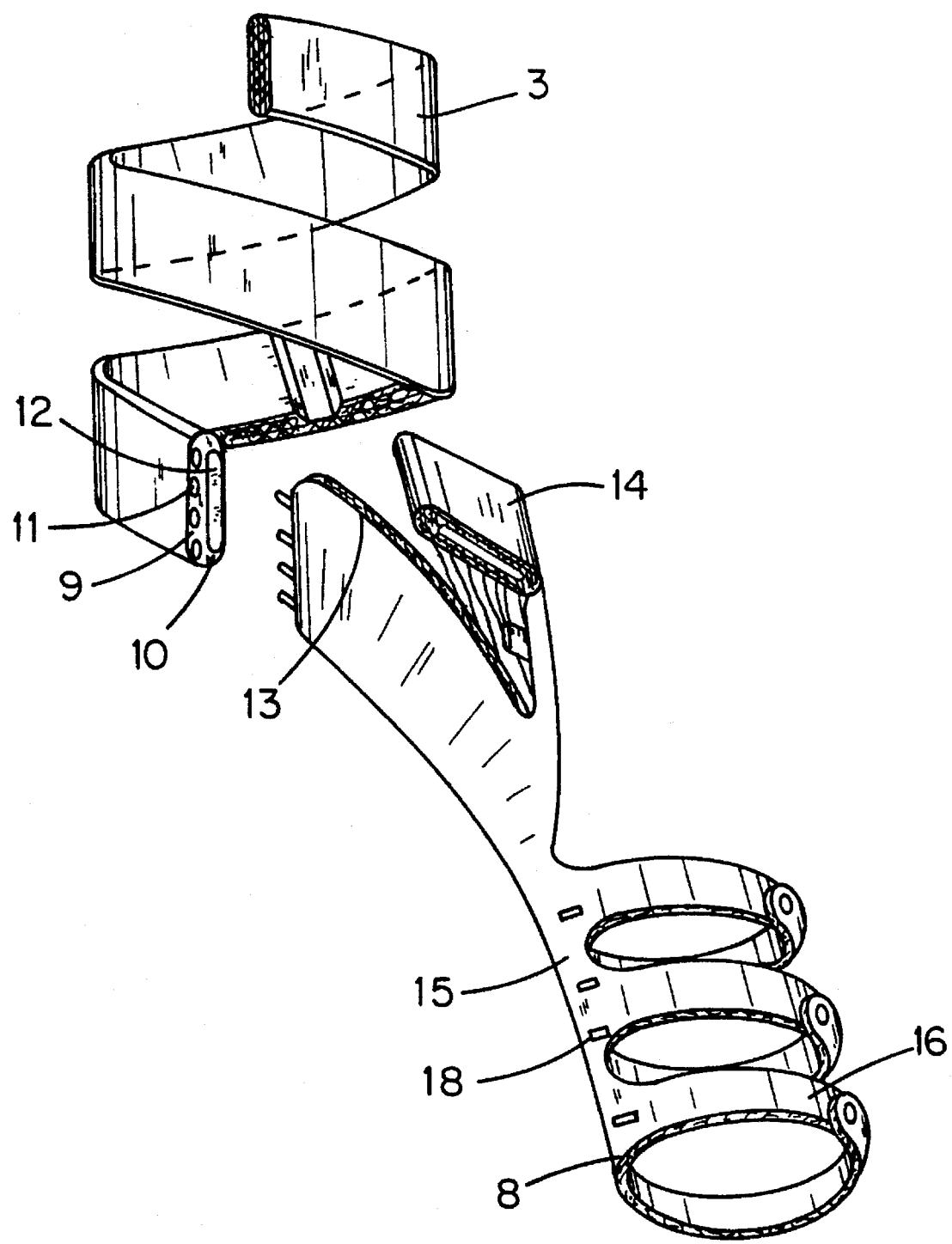
FIG. 2 is a general view of the claimed device formed of plastic reinforced with metal.
Figure 3:
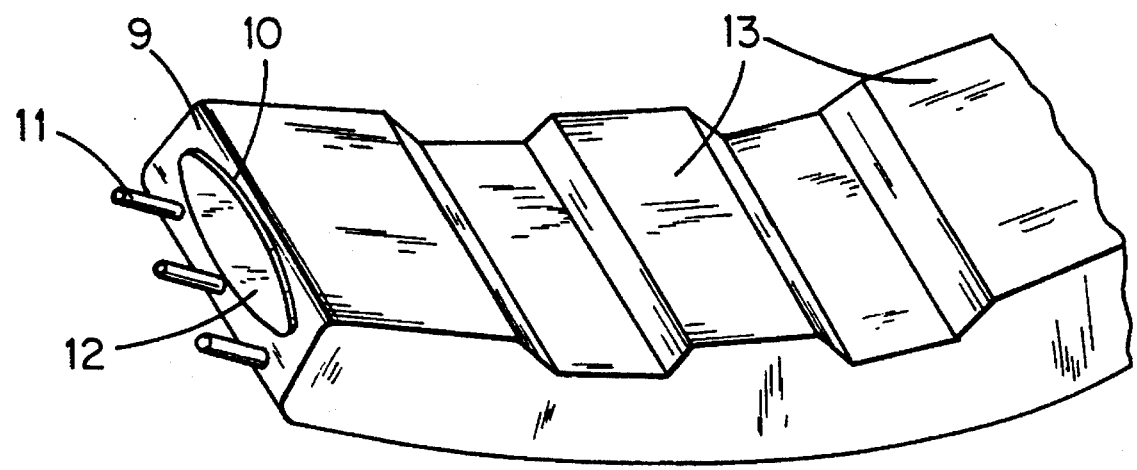
FIG. 3 is a fragmentary view of a plastic band reinforced with metal.

Another embodiment of said compressing device 1 is shown in FIG. 2. The device 1 is shaped as a band 3 of two layers 9,10 of flexible fluid-impermeable plastic. One of said layers 9 is reinforced with wire 11 formed of metal or alloy.

The layers 9,10 are peripherally sealed by welding to form a cavity 12 divided at least into two hermetically isolated chambers 13 (see FIG. 2, 3).

Said device 1 comprises a band 3 with a main compressing portion 5 disposed on the surface of said junction 2 around an insufficient valve (not shown in the drawings), an intermediate portion 6 and a fastening portion 7 as well as a means for filling said band cavity.

At least one of said plastic layers 9,10 in said band 3 is reinforced with wire 11 made of metal or alloy possessing a shape memory or spring effect.

In said compression device 1 said main compressing portion 5 of said band 3 is shaped as a Mobius band.

A quickly solidifying biologically inert fluid or biologically inert gas is applied as said means for filling said band cavity.

The band 3 in this embodiment may be as well formed of metal coated plastic, such as a "Gore-rex" type plastic.

The band 3 has an additional compressing portion 8 adjoining said main compressing portion 5 near its free end 14. The additional compressing portion 8 is made as a semirigid or resilient exovascular framework supporting and compressing the vein 4, said framework having a supporting member 15 disposed substantially along the vein longitudinal axis and compressing ribs 16,17 extending therefrom in pairs.

The additional compressing portion 8 and the band 3 form a single unit made of reinforced plastic. On the surface of the supporting member 15 notches 18 are made to define the spots of cutting off the redundant pairs of compressing ribs 16,17.

Figure 4:
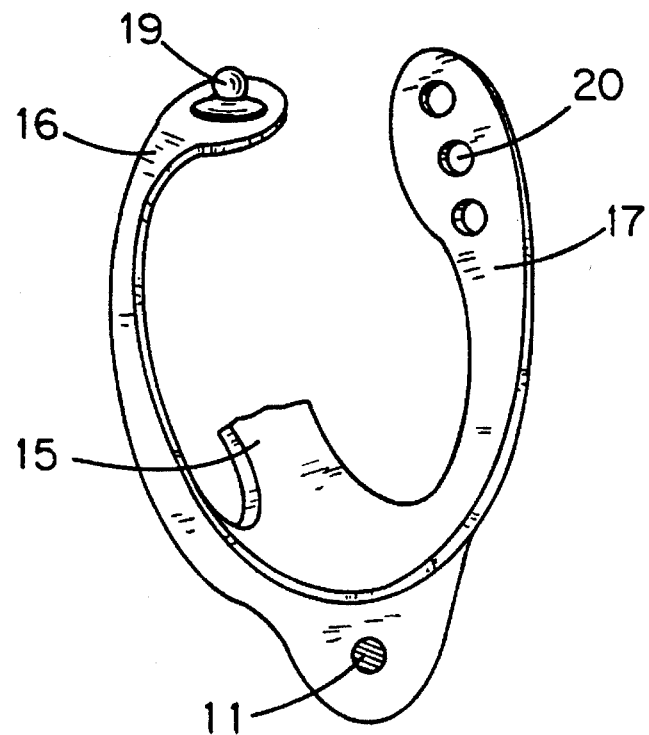
FIG. 4 is a pair of ribs of the additional compression portion.

The compressing ribs 16,17 (see FIG. 4) are provided at their ends with male 19 and female 20 connectors for mutual fastening.

Figure 5:
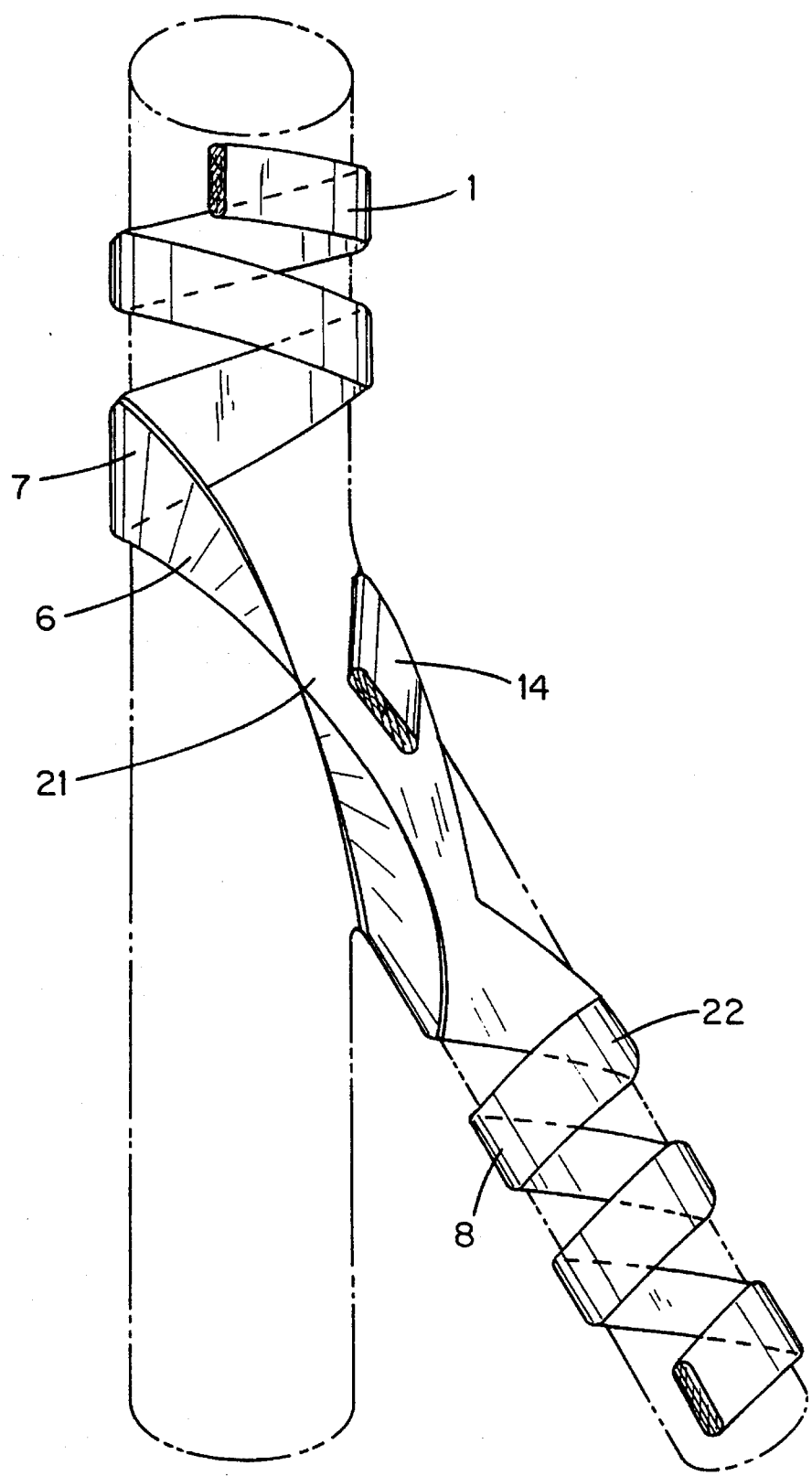
FIG. 5 is an embodiment of the claimed device shaped as a Mobius band with a bifurcated end.

In another embodiment of said device 1 the additional compressing portion 8 is shaped as a spiral band integral with the band 3 (FIG. 5).

In this case the band 3 can be shaped as a Mobius band, the bend 21 of said bend is disposed substantially in the intermediate portion 6 area. The additional compressing portion 8 is shaped as a spiral 22 of reinforced plastic and adjoins the band 3 near its free end 14.

The claimed method for external correction of insufficient valves in venous junctions based on the application of the claimed device comprises the following steps.

A venous junction 2 with one or several insufficient valves, such as the Saphen-Femoral Junction, combining the Common Femoral Vein, Superficial Femoral Vein and Great Saphene Vein are exposed by routine surgical technique. The correction device 1 is placed on said junction 2 outside so that the main compressing portion 5 may be close to the junction and fully encompass the Great Saphene Vein on the outside around the insufficient valve being in abutting contact with the Common Femoral Vein, and the fastening portion 7 being disposed substantially on the adjacent Common Femoral Vein, while the intermediate portion 6 is disposed in the area of the Common Femoral Vein and Superficial Femoral Vein connection.

The device 1, due to the spring effect of the metal band 3 or wire 11, comes into abutting contact with the surface of the venous junction 2 and adjoining veins 4 and compresses the, reducing the lumen of insufficient valves. Devices 1 wherein the band 3 or wire 11 are made of shape memory alloy operate likewise. Under the action of a human's body heat the band 3 or wire 11 restores its pre-set shape and compresses the junction 2 and veins 4. The compression force in the device 1 can be made variable in the direction from its proximal end to its distal end, previously giving the shape memory members an optimal form.

In some cases the compression force generated by metal members of the device 1—band 3 or wire 11 is sufficient for correcting the valves of said venous junction 2 since their lumen are reduced to an optimal dimension, and the normal functioning of said valves is restored.

The normal functioning of the venous junction valves is determined by the reflux value.

In case the compression force of the device 1 is insufficient the required compression force of the Great Saphene Vein insufficient valve is determined from the reflux value.

Then the vein gradual compression is performed until the reflux disappears, by injecting, via injector, a portion of a quickly solidifying biologically inert fluid into hermetically isolated chambers 13 of the band 3. This increases the rigidity of the main compressing portion 5 and the compression force transmitted to the Great Saphene Vein around its venous valve. However, the solidified fluid has a certain elasticity preventing the vein walls from injury. Instead of the quickly solidifying fluid there may be as well applied a biologically inert gas.

Subsequently the effect is checked and, if necessary, the manipulation is repeated, increasing or reducing the pressure in certain chambers 13 or in the entire cavity 12 of the band 3.

Afterwards the need in applying the additional portion of said band 8 as well as the required compression rate.

When the application of the additional compressing portion is necessary, the latter is disposed and fastened in a known manner on the Great Saphene Vein around another or several other insufficient valves, adjusting the compression rate and the length of said compressing portion, cutting off its redundant piece or the redundant end and intermediate rib pairs 16,17 in the device 1 second embodiment. Then the portion 8 is ultimately fastened on the Great Saphene Vein.

In the device 1 second embodiment it is performed by fastening in pairs the available connectors 19,20 of the ribs 16,17.

When the application of the additional portion is unnecessary, the latter is completely cut off.

After the fluid solidification in the chambers 13 or cavity 12 of the band 3 the final correction effect is checked, determining the blood reflux in the whole venous junction 2 and then closing the Saphene-Femoral Junction by routine surgical technique.

Venous valve correction in other venous junctions is performed likewise.

The claimed device and method permit to carry out a venous valve correction in venous junctions—in such places where it was impossible before due to the absence of special engineering means.

The claimed engineering solution is simple and reliable.

The correction device can be commercially produced in large quantities using the existing technology and materials such as "Gore-tex" type plastic.

In the description of the specific embodiments of the invention shown in the drawings specific terms are used. However every term specifies all equivalent members operating likewise and used to solve the same problems as the present invention.

Above we gave a description of preferred variants of the device. However, it should be clear that many improvements, changes and additions of equivalent members may be introduced without depriving the present invention of its advantages cited in the claims.

We claim:

1. A compression device for external correction of insufficient valves in venous junctions, said device being adapted for placement substantially around the junction with insufficient valves in abutting contact with a desired area of said junction, comprising:

a band adapted to be disposed around at least two veins of said junction and possessing a different rigidity and compressing force in the direction from a proximal end to a distal end thereat, said band including:

at least one main compressing portion adapted to be disposed on a vein surface of said junction around the insufficient valve;

an intermediate portion disposed adjacent said at least one main compressing portion;

a fastening portion disposed adjacent said intermediate portion; and means disposed adjacent the band for protecting the vein surface from injury.

2. A compression device according to claim 1, wherein said band is shaped as a Mobius band.

3. A device according to claim 1, wherein said band includes at least one additional compressing portion adjoining said main compressing portion, said additional compressing portion being disposed on an insufficient vein around at least another insufficient valve near said junction.

4. A device according to claim 3, wherein said main and additional compressing portions are each formed as a bifurcated end of said band.

5. A compression device for external correction of insufficient valves and adapted for placement substantially around a junction with insufficient valves in abutting contact with a desired area of said junction, comprising: a plastic coated band of at least one of metal and alloy encompassing at least two veins of said junction and possessing a different rigidity and compressing force in the direction from a proximal end to a distal end thereof, said band comprising:

at least one main compressing portion adapted to be disposed on a vein surface of said junction around the insufficient valve;

an intermediate portion disposed adjacent said at least one main compressing portion; and a fastening portion disposed adjacent said intermediate portion.

6. A compression device according to claim 5, wherein said main compressing portion of said band is shaped as a Mobius band.

7. A device according to claim 5, wherein said band has at least one additional compressing portion adjoining said main compressing portion, said additional compressing portion adapted to be disposed on an insufficient vein around at least another insufficient valve near said junction and formed as at least one of a semirigid and a resilient exovascular framework supporting and compressing the vein, said framework including a supporting member disposed substantially along a longitudinal axis of the vein and compressing ribs, extending from the supporting members and male and female connector means for fastening said ribs together.

8. A device according to claim 7, wherein said main additional compressing portions are each formed as a bifurcated end of said band.

9. A device according to claim 5, wherein said band is formed of metal with a spring effect.

10. A device according to claim 5, wherein said band is formed of a shape memory alloy.

11. A device according to claim 5, wherein said band is coated with a "Gore-tex" type plastic.

12. A compression device for external correction of insufficient valves in venous junctions, adapted for placement substantially around a junction surface with insufficient valves in abutting contact with a desired area of said junction surface, comprising: a band of at least two layers of flexible fluid-impermeable plastic peripherally sealed together to form a band cavity having at least one hermetically isolated chamber, said band adapted to encompass at least two veins of said junction and possessing different rigidity and compressing force in the direction from a proximal end to a distal end thereof, said band including:

at least one main compressing portion disposed on the surface of said junction around the insufficient valve, an intermediate portion disposed adjacent said main compressing portion and a fastening portion disposed adjacent said intermediate portion; and a material filling said band cavity to provide for vein compression and prevent reflux.

13. A compression device according to claim 12, wherein at least one of said plastic layers in said band is reinforced with at least one of a shape memory metal and an alloy.

14. A compression device according to claim 12, wherein said main compressing portion of said band is formed as a Mobius band including said at least two layers of flexible fluid-impermeable plastic peripherally sealed together, at least one of said plastic layers being reinforced with at least one of a metal and an alloy.

15. A device according to claim 12, wherein said material filling said band cavity includes at least one of a quickly solidifying biologically inert fluid and a biologically inert gas.

16. A device according to claim 12, wherein said band is formed of a plastic reinforced with metal.

17. A device according to claim 12, wherein said band has at least one additional compressing portion adjoining said main compressing portion proximate a free end thereof, said additional compressing portion adapted to be disposed on the insufficient vein around at least another insufficient valve near said junction and formed of at least one plastic layer.

18. A device according to claim 17, wherein at least one layer of said additional compressing portion is reinforced with metal.

19. A device according to claim 17, wherein the additional compressing portion is formed of at least another two plastic layers peripherally sealed together to form a second cavity having at least one hermetically isolated chamber.

20. A device according to claim 17, wherein said main and additional compressing portions are each shaped as a bifurcated end of said band.

21. A device according to claim 17, wherein said additional compressing portion is formed as at least one of a semirigid and a resilient exovascular framework adapted to support and compress the vein, said framework having a supporting member disposed substantially along the vein longitudinal axis and compressing ribs extending therefrom, and male and female connector for fastening said ribs together.

22. A method for external correction of insufficient valves in venous junctions, comprising the steps of:

a) surgically exposing the venous junction;

b) placing a correction device on the venous junction so that a main compressing portion of said correction device is sufficiently close to the junction to fully encompass a vein located outside around the insufficient valve, and a fastening portion of the device is disposed substantially on an adjacent vein;

c) determining blood reflux in the vein with an insufficient valve;

d) performing a gradual compression of the vein until the reflux disappears, by injecting a portion of at least one of a biologically inert gas and a quickly solidifying biologically inert fluid into hermetically isolated chambers of said correction device;

e) repeating step (d) by increasing or reducing compressing in certain chambers of said band;

f) determining a need for applying an additional compressing portion of said correction device;

g) when application of said additional compressing portion is necessary, disposing and fastening the latter on the vein adjusting the compression rate and said portion length, cutting off a redundant piece of same, and fastening together connectors of said additional compressing portion;

h) when application of said additional compressing portion is not necessary, cutting off the entire said additional compressing portion;

i) checking the final correction effect, determining the blood reflux in the entire junction being corrected; and j) closing the wound by routine technique.

* * * * *